(12) United States Patent
Brown

(10) Patent No.: US 8,638,428 B2
(45) Date of Patent: Jan. 28, 2014

(54) METHOD AND APPARATUS FOR USING OPTICAL FEEDBACK TO DETECT FIBER BREAKDOWN DURING SURGICAL LASER PROCEDURES

(76) Inventor: Joe Denton Brown, Panama City, FL (US)

( * ) Notice: Subject to any disclaimer, the term of this patent is extended or adjusted under 35 U.S.C. 154(b) by 173 days.

(21) Appl. No.: 13/150,573

(22) Filed: Jun. 1, 2011

(65) Prior Publication Data

US 2011/0292378 A1      Dec. 1, 2011

Related U.S. Application Data

(60) Provisional application No. 61/350,301, filed on Jun. 1, 2010.

(51) Int. Cl.
*G01N 21/00*    (2006.01)

(52) U.S. Cl.
USPC ............................................. 356/73.1

(58) Field of Classification Search
USPC ............................................. 356/73.1
See application file for complete search history.

(56) References Cited

U.S. PATENT DOCUMENTS

| | | | |
|---|---|---|---|
| 3,912,362 A | 10/1975 | Hudson | |
| 4,060,308 A | 11/1977 | Barnoski et al. | |
| 4,385,832 A | 5/1983 | Doi et al. | |
| 4,474,429 A | 10/1984 | Yoidas et al. | |
| 4,519,390 A | 5/1985 | Horne | |
| 4,543,477 A | 9/1985 | Doi et al. | |
| 4,575,181 A | 3/1986 | Ishikawa | |
| 4,669,465 A | 6/1987 | Moore et al. | |
| 4,678,273 A | 7/1987 | Vilhelmsson | |
| 4,718,417 A | 1/1988 | Kittrell et al. | |
| 4,737,011 A | 4/1988 | Iri et al. | |
| 4,760,845 A | 8/1988 | Kovalcheck | |
| 4,762,385 A | 8/1988 | Fuse | |
| 4,784,466 A | 11/1988 | Khoe et al. | |
| 4,832,024 A | 5/1989 | Boussignac et al. | |
| 4,883,054 A | 11/1989 | Fuller et al. | |
| 4,883,342 A | 11/1989 | Ishii et al. | |
| 4,913,142 A | 4/1990 | Kittrell et al. | |
| 4,994,059 A | 2/1991 | Kosa et al. | |
| 5,057,099 A | 10/1991 | Rink | |
| 5,061,265 A | 10/1991 | Abela et al. | |
| 5,098,427 A | 3/1992 | Hessel et al. | |
| 5,101,457 A | 3/1992 | Blonder et al. | |
| 5,132,079 A | 7/1992 | Stewart | |
| 5,154,707 A | 10/1992 | Rink et al. | |
| 5,179,610 A | 1/1993 | Milburn et al. | |
| 5,196,005 A | 3/1993 | Doiran et al. | |
| 5,219,345 A | 6/1993 | Potter | |
| 5,243,681 A | 9/1993 | Bowen et al. | |
| 5,274,721 A | 12/1993 | Dickinson et al. | |
| 5,291,570 A | 3/1994 | Filgas et al. | |
| 5,299,141 A | 3/1994 | Hungerford et al. | |

(Continued)

*Primary Examiner* — Tu Nguyen
(74) *Attorney, Agent, or Firm* — Bacon & Thomas, PLLC

(57) ABSTRACT

Failure events detected by a laser surgery monitoring feedback circuit are analyzed in order to distinguish between events that result from fiber breakdown and those arising from other sources, such as burning of tissues. If the number of failure events within a predetermined time exceeds a predetermined count, then it is determined that the radiation is the result of fiber breakdown. If the number of failure events within the predetermined time is less than the predetermined count, then it is determined that the failure events result from other causes, such as heating of tissues by the laser. Based on the analysis, an override switch or alarm may be initiated.

6 Claims, 1 Drawing Sheet

(56) References Cited

U.S. PATENT DOCUMENTS

| | | | |
|---|---|---|---|
| 5,300,066 | A | 4/1994 | Manoukian et al. |
| 5,330,465 | A | 7/1994 | Dorian et al. |
| 5,354,323 | A | 10/1994 | Whitebook |
| 5,490,227 | A | 2/1996 | Tanabe et al. |
| 5,565,976 | A * | 10/1996 | Fieggen et al. ............ 356/39 |
| 5,569,240 | A | 10/1996 | Dowlatshahi et al. |
| 5,619,602 | A | 4/1997 | Sandstrom et al. |
| 5,649,923 | A | 7/1997 | Gregory et al. |
| 5,820,627 | A | 10/1998 | Rosen et al. |
| 5,829,445 | A | 11/1998 | Martin et al. |
| 5,928,222 | A | 7/1999 | Kleinerman |
| 5,946,437 | A | 8/1999 | Uchida et al. |
| 5,968,033 | A | 10/1999 | Fuller et al. |
| 6,154,596 | A | 11/2000 | Ionov |
| 6,282,349 | B1 | 8/2001 | Griffin |
| 6,389,307 | B1 | 5/2002 | Abela |
| 6,398,777 | B1 | 6/2002 | Navarro et al. |
| 7,204,645 | B2 | 4/2007 | Brown |
| 7,212,492 | B1 * | 5/2007 | Au et al. ............ 370/229 |
| 2002/0045811 | A1 | 4/2002 | Kittrell |
| 2002/0068963 | A1 | 6/2002 | Maki et al. |
| 2003/0023236 | A1 | 1/2003 | Gowda et al. |
| 2004/0006333 | A1 | 1/2004 | Arnold et al. |
| 2004/0092913 | A1 | 5/2004 | Hennings et al. |
| 2004/0147912 | A1 | 7/2004 | Sinofsky |
| 2004/0147913 | A1 | 7/2004 | Sinofsky |
| 2004/0162490 | A1 | 8/2004 | Soltz et al. |
| 2004/0249261 | A1 | 12/2004 | Torchia et al. |
| 2005/0038419 | A9 | 2/2005 | Arnold et al. |
| 2005/0124985 | A1 | 6/2005 | Takayama et al. |
| 2005/0131400 | A1 | 6/2005 | Hennings et al. |
| 2005/0267452 | A1 | 12/2005 | Farr et al. |
| 2005/0273090 | A1 | 12/2005 | Nieman et al. |
| 2005/0288654 | A1 | 12/2005 | Nieman et al. |
| 2005/0288655 | A1 | 12/2005 | Root et al. |
| 2006/0052661 | A1 | 3/2006 | Gannot et al. |
| 2006/0122587 | A1 | 6/2006 | Sharareh |
| 2006/0217692 | A1 | 9/2006 | Nauberger |
| 2006/0217693 | A1 | 9/2006 | Gowda et al. |
| 2006/0253178 | A1 | 11/2006 | Masotti |
| 2007/0167937 | A1 | 7/2007 | Brown |
| 2009/0062782 | A1 | 3/2009 | Brown |
| 2009/0149845 | A1 | 6/2009 | Brown |
| 2009/0177191 | A1 | 7/2009 | Brown |

* cited by examiner

METHOD AND APPARATUS FOR USING OPTICAL FEEDBACK TO DETECT FIBER BREAKDOWN DURING SURGICAL LASER PROCEDURES

This application claims the benefit of U.S. provisional application Ser. No. 61/350,301, filed Jun. 1, 2010.

BACKGROUND OF THE INVENTION

1. Field of the Invention

The invention relates to a method and apparatus for distinguishing between flashes or other failure events that result from fiber breakdown and those arising from other sources, such as burning of tissues, during a laser surgical procedure.

2. Description of Related Art

U.S. patent application Ser. No. 61/006,077 (Publication Nos. 2009/0149845 and 2009/0177191) and U.S. patent application Ser. No. 11/714,785 (Publication No. 2007/0167937) describe optical feedback systems designed to prevent thermal runaway of a fiber tip when contaminated with biological tissues including blood by detecting damage radiation emitted during burning or overheating of the fiber tip. This thermal runaway can cause adverse effects such as pain, nerve damage, adjacent tissue damage, vein perforation and creation of toxic fumes. A commercial example of such a system if the LaserGuard™ system offered by Optical Integrity, Inc. of Panama City, Fla.

In some applications, such as removal of stones from the urinary tract, it may be difficult for the feedback system to distinguish between failure events caused by fiber breakdown, and failure events from other sources, such as heating of the stone. This can cause premature shutdown of the laser if the failure events are not the result of fiber breakdown, or damage resulting from a burning fiber tip if the failure events are ignored even though they are the result of fiber breakdown.

SUMMARY OF THE INVENTION

To solve the problem of distinguishing between failure events, a circuit is added to the feedback system that delays shutdown for a predetermined count. If the number of failure events within a predetermined time exceeds a predetermined count, then it is determined that the radiation is the result of fiber breakdown. If the number of failure events within the predetermined time is less than the predetermined count, then it is determined that the failure events result from other causes, such as heating of tissues by the laser. By way of example and not limitation, the predetermined count might be five or six counts.

This system is particularly useful for distinguishing radiation emitted as a result of fiber breakdown from failure events originating from stones. Since the stones move around, any failure events originating from the stones will be temporary.

The system may be applied to the feedback systems described in the above-cited patent applications, in the LaserGuard™ system, or in any other optical feedback system capable of detecting damage radiation during a laser surgical procedure.

In order to enable a clinician to control shutdown of the laser in order to adapt to different circumstances and requirements, the number of counts used to trigger shutdown may be made adjustable, and/or an audible or visual warning may be triggered at a predetermined count before actual shutdown occurs.

DETAILED DESCRIPTION OF PREFERRED EMBODIMENTS

Figure 2:
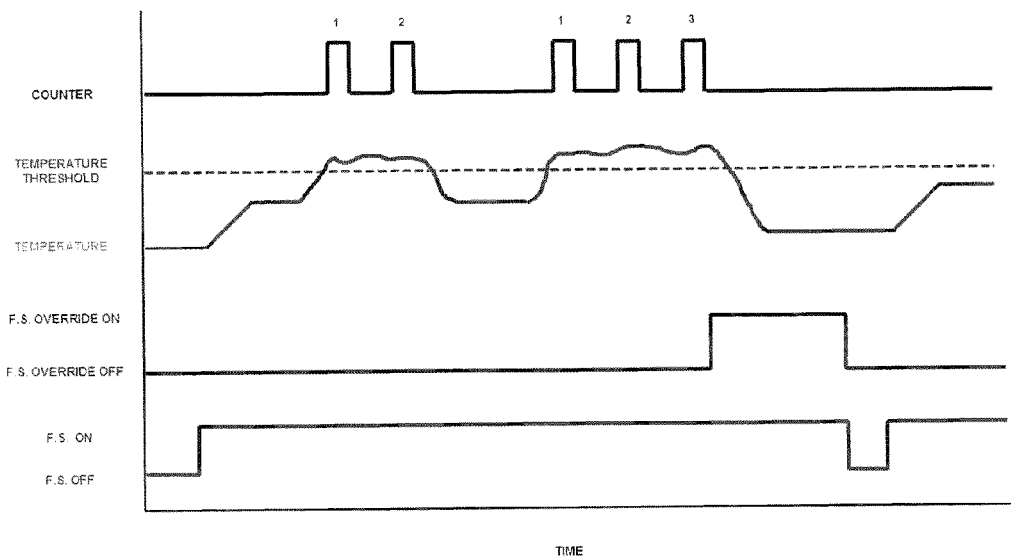
FIG. 2 is a functional block diagram of the apparatus whose operation is illustrated in FIG. 1.

As illustrated in FIG. 2, the system and method of the invention includes a detector 1. Detector 1 may be an optical feedback detector associated with a laser 2 and laser delivery fiber 3 so as to detect radiation originating in the area of a laser delivery target 4 and indicative of a possible failure event. The radiation may be detected through the laser delivery fiber 3 or directly, depending on the location of the detector. Alternatively, detector 1 maybe a non-optical detector, such as a temperature sensor, located near the target 4. The detector 1 is connected to a microcontroller that counts potential failure events and activates a switch 7 to override the manual laser control switch 6 and shut down the laser if the count is indicative of an actual failure of the fiber or damage-inducing thermal runaway.

Figure 1:
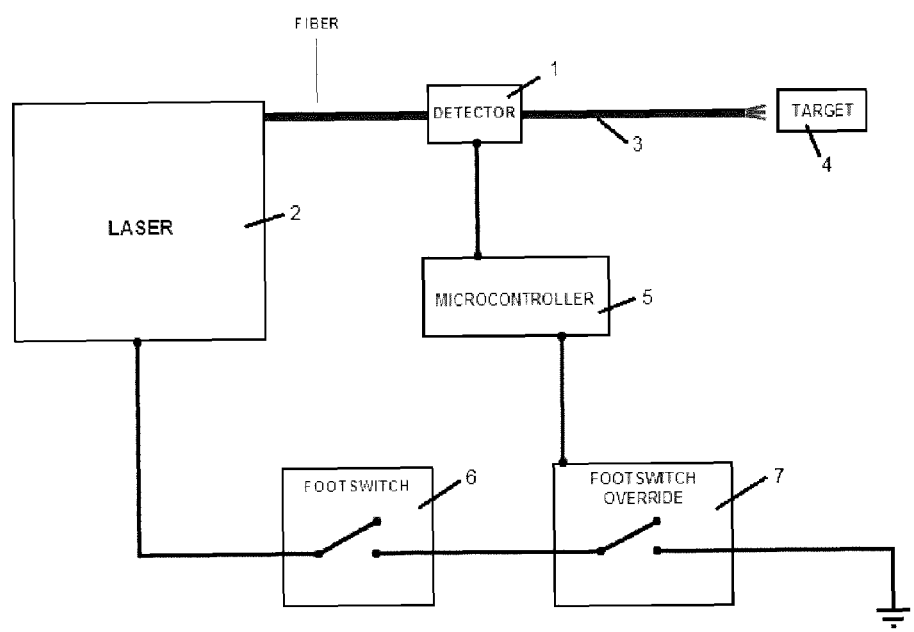
FIG. 1 is a signal timing diagram illustrating operation of the apparatus and method of a preferred embodiment of the invention.

FIG. 1 illustrates the manner in which the method and system of the invention distinguishes between potential failure events in order to determine if override and shutdown of the laser is required. The output of the detector 1 is analyzed to determine if a potential failure event has occurred. For example, the output of the detector 1 may be a temperature reading (either a direct temperature reading or an analysis of optical feedback that indicates temperature or thermal runaway). This output is indicated in FIG. 1 by the line labeled "temperature." The detector output is then compared with a threshold indicative of a potential failure event, and a counter is started when the threshold is exceeded. If the temperature falls below the threshold, then the count is stopped. If the count within a predetermined time period is less than two, in the illustrated example, then no action is taken. However, if the count within the predetermined time period exceeds three, then the override switch 7 is activated to at least temporarily stop operation of the laser. The number of counts required to activate the switch 7 is preferably adjustable.

The state of the override switch 7 is indicated in FIG. 2 by the lines F.S. OVERRIDE ON and F.S. OVERRIDE OFF. In addition, FIG. 2 shows possible states of foot switch 6, indicated by F.S. ON and F.S. OFF. As illustrated, when the manual switch 6 is deactivated, the override switch 7 no longer is required, and manual reactivation of the switch 6 can occur whenever the laser operator determines reactivation to be appropriate.

In addition to or instead of overriding the manual switch 6, the microcontroller 5 may be programmed to initiate an alarm or warning. The alarm or warning may occur at a count that is different than the one resulting in override, for example, each time the threshold is exceeded, at a count that is less than the count required to initiate an override, or when the threshold has been exceeded a predetermined number of times even if a failure event has not occurred.

It will be appreciated by those skilled in the art that the number of counts required for activation of the override switch 7, or for otherwise taking action in response to determination that an actual failure event has occurred, is not limited to three. In addition, it is not required that failure event detection rely on discrete counts within a predetermined time period. Instead of or in addition to the illustrated counting procedure, failure detection could be based on an absolute total number of counts, on a time that the threshold is exceeded, or on some other method of analyzing the detector output. In addition, the laser may be controlled by means other than a footswitch and footswitch override. These and other variations and modifications are intended to be included within the scope of the invention.

I claim:

1. A method of distinguishing between failure events resulting from fiber breakdown and failure events resulting from other sources, said failure events being detected by an optical feedback system during a laser surgical procedure, comprising the steps of:

during the laser surgical procedure, activating a laser for delivering surgical laser energy through an optical fiber;

monitoring the optical feedback system connected to surgical laser apparatus in order to detect said failure events;

upon detecting said failure events through the optical feedback system, activating a counter; and deactivating the laser and/or initiating a warning when a predetermined count has been reached, the predetermined count indicating that the detected failure events result from breakdown of the optical fiber.

2. The method of claim 1, wherein said predetermined count is adjustable.

3. The method of claim 1, wherein the step of deactivating the laser and/or initiating a warning occurs when the predetermined count has been reached within a predetermined period of time.

4. Apparatus for distinguishing between failure events resulting from fiber breakdown and failure events resulting from other sources, said failure events being detected by an optical feedback system during a laser surgical procedure carried out by activating a laser to emit laser energy through an optical fiber and monitoring the laser surgical procedure through the optical feedback system, comprising:

a counter associated with the optical feedback system for counting said failure events detected by the optical feedback system during the laser surgical procedure;

circuitry for deactivating the laser and/or initiating a warning when a predetermined count of the failure events detected by the optical feedback system has been reached by said counter, the predetermined count indicating that the failure events detected by the optical feedback system are failure events resulting from breakdown of the optical fiber.

5. Apparatus as claimed in claim 4, wherein said predetermined count is adjustable.

6. Apparatus as claimed in claim 4, wherein the step of deactivating the laser and/or initiating a warning occurs when the predetermined count has been reached within a predetermined period of time.

* * * * *